United States Patent [19]
Latulippe et al.

[11] Patent Number: 5,599,512
[45] Date of Patent: Feb. 4, 1997

[54] STERILIZATION SUPPORT AND STORAGE CONTAINER SYSTEM

[75] Inventors: Michael L. Latulippe, Derry, N.H.; Albert A. Lepage, Jr., Norton, Mass.

[73] Assignee: Poly Vac, Incorporated, Manchester, N.H.

[21] Appl. No.: 635,287

[22] Filed: Apr. 19, 1996

Related U.S. Application Data

[63] Continuation of Ser. No. 438,604, May 10, 1995, abandoned.

[51] Int. Cl.$^6$ .............................. A61L 2/26; F16B 21/04; F16B 19/00; F16B 13/00
[52] U.S. Cl. .................... 422/300; 422/310; 206/438; 24/453; 24/704.1; 411/509; 411/913
[58] Field of Search ......................... 422/297, 300, 422/310; 206/438, 439, 635, 487, 560, 562, 563; 24/289, 297, 453, 704.1; 411/508, 509, 913

[56] References Cited

U.S. PATENT DOCUMENTS

| | | | |
|---|---|---|---|
| 3,908,235 | 9/1975 | Telliard et al. | 411/508 |
| 4,135,868 | 1/1979 | Schainholz | 422/300 |
| 4,551,110 | 11/1985 | Selvage et al. | 411/509 |
| 4,798,292 | 1/1989 | Hauze | 422/300 |
| 4,953,269 | 9/1990 | Ragsdale | 24/704.1 |
| 4,973,212 | 11/1990 | Jacobs | 411/508 |
| 5,098,676 | 3/1992 | Brooks, Jr. | 422/292 |
| 5,143,500 | 9/1992 | Schuring et al. | 411/508 |
| 5,184,377 | 2/1993 | Ragsdale et al. | 24/704.1 |
| 5,381,896 | 1/1995 | Simons | 206/370 |
| 5,384,103 | 1/1995 | Miller | 422/300 |

OTHER PUBLICATIONS

"Multipak The Bright New Star in Instrument Handling" Riley Medical, Inc. company brochure.
Endo Pak "simple, Versatile Protection" Riley Medical, Inc. company brochure.
Scope Pak "Ultimate Protection" Riley Medical, Inc. company brochure.
"Laparoscopic Instrument Sterilization Systems" PolyVac Incorporated company brochure.
Multipak Standardized Instrument Organizing System Riley Medical, Inc. company brochure.

*Primary Examiner*—Robert J. Warden
*Assistant Examiner*—E. Leigh Dawson
*Attorney, Agent, or Firm*—Hayes, Soloway, Hennessey, Grossman & Hage, P.C.

[57] ABSTRACT

A support for medical instruments is provided to securely grasp the instrument during sterilization and storage. The support can be readily rearranged on a sterilization tray and can be securely locked in whatever position is desired. It employs a novel arrangement of locking bayonet fingers and a simple removal tool for changing location of the support.

9 Claims, 2 Drawing Sheets

5,599,512

1

STERILIZATION SUPPORT AND STORAGE CONTAINER SYSTEM

This is a continuation of application Ser. No. 08/438,604 filed on May 10, 1995, now abandoned.

BACKGROUND OF THE INVENTION

In the sterilization of surgical instruments it is desirable to have a sterilization tray assembly which will support the instruments during sterilization and can also be used for transporting and storing the instruments after sterilization. As instruments become larger and more complex, such as those used in endoscopy and orthoscopic procedures, it is necessary to provide a support having resilient contact with the surgical instrument and which can be securely positioned within the tray so that it will not be displaced during handling of the tray. Due to the appreciable weight and size of the surgical instruments this support may be subjected to considerable stress.

Since surgical instruments come in a wide variety of shapes and forms, and since it is impractical to have a single tray devoted to a particular type of surgical instrument, the art has developed numerous systems wherein supports for the surgical instruments can be provided in modular form and the various modules can be selectively positioned within the tray, for example, by plugging portions of the support elements through holes in a portion of the tray. The support elements can thus be arranged to match the shape of the surgical instrument to be sterilized.

Examples of such products are shown in U.S. Pat. No. 4,135,868 to Sheinholz and U.S. Pat. No. 5,384,103 to Miller. Similar products are commercially available from companies such as Poly-Vac, Incorporated, of Manchester, N.H., and other suppliers. Some of these prior devices include integrally molded stubs, for example positioned on the bottom of the flexible inserts, which stubs can be locked into the vent holes in the tray as shown, for example, in FIG. 1 of Miller U.S. Pat. No. 5,384,103. They may also comprise separate, more rigid, holding elements such as shown in FIG. 3 of the above '103 patent where a rigid holder for the support element is be fastened by screws to the tray or an additional shelf carried by the tray. In the '868 patent, the support element for a soft sponge rubber, constituting a hold down pad, is supported by a channel member having outwardly extending buttons which can be forced into vent holes in the cover or base of the sterilizing tray. Another prior U.S. patent of interest, U.S. Pat. No. 4,798,292 shows hollow pegs having elongated legs which can be used for attachment to a perforated sterilizer tray.

While all of the systems described in the prior patents and commercially available products provide a certain amount of flexibility, they do not provide both strong security for the support members and low cost. Nor do they allow for ease of removal of a securely mounted support so that the supports can be differently positioned in the sterilization trays for holding different shapes of surgical instruments to be sterilized.

SUMMARY OF THE INVENTION

It is thus an object of the present invention to overcome the aforesaid and other disadvantages of the prior art. In the present invention the elements for clasping the surgical instruments are formed of resilient deformable members, as is well known in the art. These deformable members are secured within relatively rigid, strong, plastic support elements. These relatively rigid support elements have integrally formed fastening means which extend downwardly from the bottom surface of the support elements and have a size and shape designed to penetrate selected vent holes in the cover, base or support structure forming a part of the sterilization tray system. These fastening means lock the relatively rigid support element in a desired location. In addition, the fastening means are designed so that they can be readily removed by a simple tool which engages the ends of the fastening means and pushes them back through the holes in which they were previously securely locked in position.

BRIEF DESCRIPTION OF THE DRAWINGS

Yet other objects and advantages of the present invention will be apparent from the following detailed description of the invention, taken in conjunction with the accompanying drawings wherein like numbers depict like parts, and wherein.

DETAILED DESCRIPTION OF THE INVENTION

Figure 1:
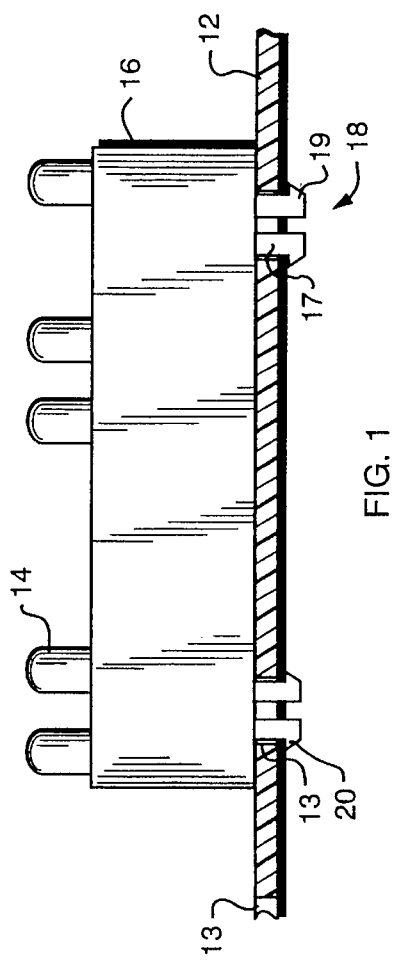
FIG. 1 is a schematic, partially sectional diagramatic view of a portion of the sterilization tray which can be either the bottom, or top or insert tray, in a sterilization tray system of the type well known in the prior art.
Figure 3:
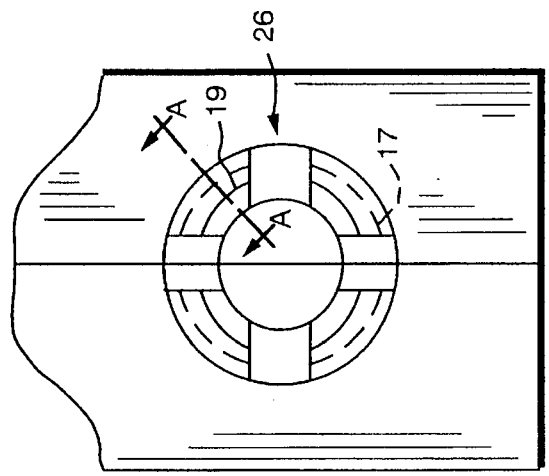
FIG. 3 is a schematic, partially sectional view of FIG. 2 showing the relationship of the fastening means and their heads with the tray removed and the fastening means in normal position.
Figure 2:
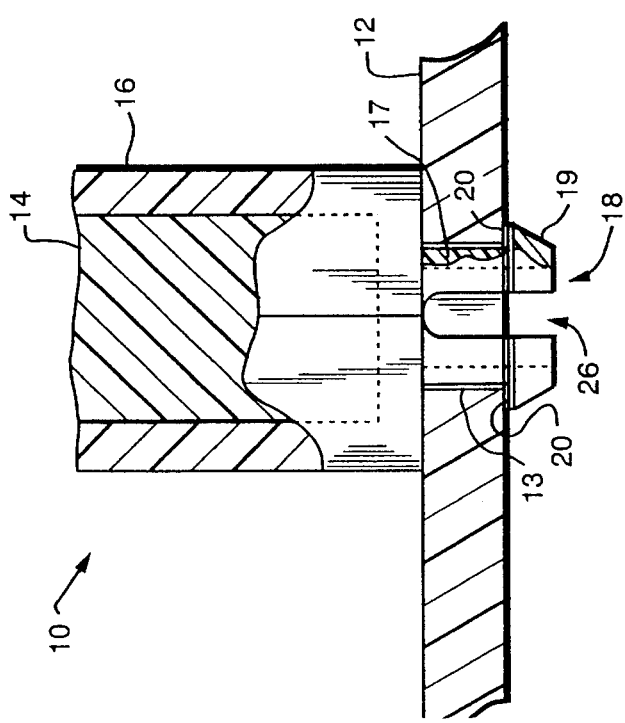
FIG. 2 is an enlarged, schematic, partially sectional view of the fastening means and their relationship to the vent hole in the tray.

Referring now to FIGS. 1, 2 and 3 the sterilization tray element generally indicated at 10 may be any of the components of a sterilization system well known in the prior art. It can be a cover, bottom or separate shelf in the tray. A portion of this element 12 has a number of vent holes 13 for passage of sterilization fluids, as is well known in the art. Resilient clamp members, of any type well known in the art and which can take many shapes, are illustrated schematically at 14 as being carried by a support 16. From the bottom of the support 16 are downwardly extending elongated fingers 17 which terminate in enlarged heads 18.

Each enlarged head 18 has a conical end 19 and flat shoulder 20. As can be seen in the right hand side of FIG. 2, (which is partial sectional view along the line AA of FIG. 3,) the finger 17 is relatively thin and terminates in the shoulder 20. This shoulder is the back side of the external head 18. As can be seen, the shoulder 20 extends outwardly from the exterior portion of the finger 17. The fingers 17 are arcuate sections separated by spaces 26, thus providing necessary resilience to the fingers 17. When this set of fingers 17 is pushed down through the hole 13, each finger is moved radially by the conical surface 19 towards the axis of the hole so that each head 18 passes through the hole 13. The resilience of the finger 17 snaps the head outwardly and the shoulder 20 engages the backside of tray element 12. The arrangement of the fingers 17 and their enlarged heads 18 and shoulders 20 firmly secures the support 16 with respect to the tray 12 so that it is essentially impossible to accidentally remove support 16 from the tray, despite rough handling, dropping, etc.

Figure 4B:
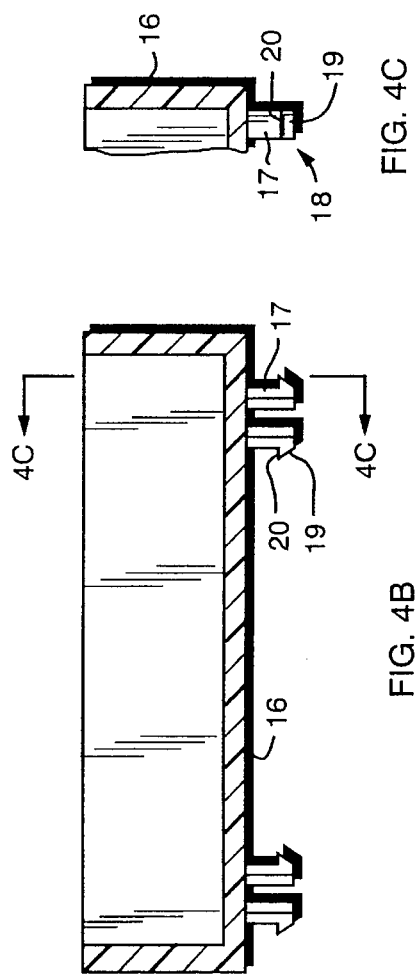
FIGS. 4A, 4B and 4C are respectively top, side, and cross-sectional views of a half section of the support element 16 showing the fingers 17 and heads 18.
Figure 4C:
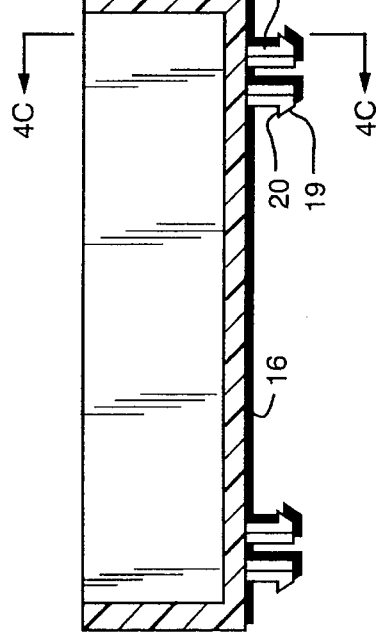
Figure 4A:

In a preferred form of the invention the clamping member 14 is made of a resilient sterilizable material such as a synthetic rubber, as is well known in the medical art. The support element 16 is preferably molded from high impact strength semi-rigid medical grade, polymeric material or the like. Preferably, the two sets of four fingers 17 are integrally molded into the support elements 16 as shown in FIGS. 4A, 4B and 4C and are small arcs of a cylinder having about the same external diameter as hole 13. Preferably clamping member 14 is molded to shape and then positioned between two halves of the support element 16 and the whole assembly is affixed together, e.g. by means of ultrasonic welding. Alternatively, the assembly may be affixed together by adhesive means or by mechanical fastening means.

Figure 5:
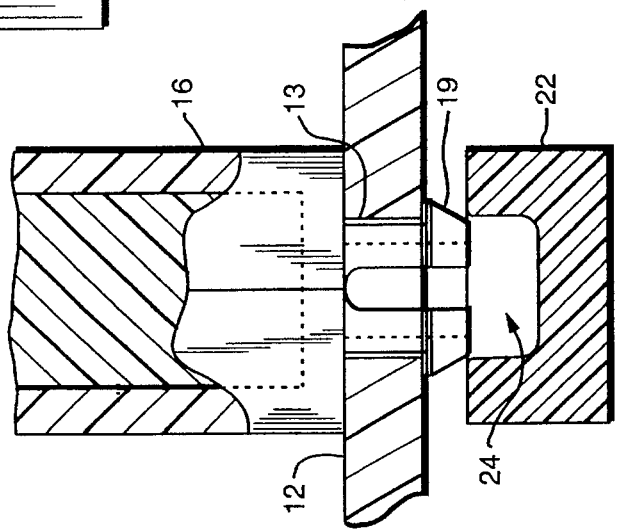
FIG. 5 is a schematic partially sectional view showing the relationship of a removal tool forming a part of this invention and one of the heads of the fastening means.

When it is desired to remove the support 16 for repositioning, for example a removal tool 22 is pressed against the head 18 of the fingers 17. This removal tool is shown in position in FIG. 5. Tool 22 preferably has an opening 24 slightly smaller than the size of the hole 13 in which the elongated fingers are locked. As the tool is moved upwardly, as seen in FIG. 5 against the conical surface 19 the slight taper 23 at the top of opening 24 in the removal tool engages the conical surface 19 and moves the head 18 towards the axis of the hole. Since the opening 24 is slightly smaller than the hole 13 it will compress the ends of the elongated fingers towards each other so that they have a compressed size smaller than hole 13. When the tool 22 finally is seated against the bottom of tray 12, the shoulders 20 will be moved out of engagement with the bottom surface of tray element 10 and the support element 16 can be easily detached from the tray.

While one preferred arrangement of fastening means is illustrated above, numerous modification thereof can be made without departing from the spirit of the invention. For example the fingers 17 can be planar rather than arcuate and the heads 18 can be triangular rather than conical. This latter arrangement would be preferable where the hole 13 is rectangular rather than circular. In this case the opening 24 in the tool 22 would be a slot slightly narrower than hole 13.

We claim:

1. In a combination including a sterilization tray assembly for sterilizing surgical instruments, said assembly including a structure having a plurality of holes and a resiliently deformable member for clasping surgical instruments; the improvement comprising a relatively rigid plastic support element connected to said deformable member and being for predeterminedly positioning said resiliently deformable member with respect to different holes in said structure, and said relatively rigid support element has integrally formed fastening means including fingers having respective tapered heads and downwardly extending from a bottom surface of said support element and positioned to penetrate predetermined holes of said structure to lock said support element in position, said combination also including a removal tool for releasing said fingers from predetermined holes into which said fingers have penetrated, said tool including an opening adapted and operatively positioned to engage the tapered head on each said finger when said fingers penetrate said predetermined holes whereby to deform said fingers to release said fingers from said predetermined holes, said opening being slightly smaller than said hole.

2. The combination of claim 1, wherein said fastening means comprises at least two fingers.

3. The combination of claim 1, wherein said fastening means have tapered ends.

4. The combination of claim 3, wherein said tapered ends are conically shaped.

5. The combination of claim 1, wherein said fastening means comprises at least two fingers having partial conical surfaces, and the holes in the structure and the opening of the tool are both circular.

6. The combination of claim 1, wherein said fingers also include surfaces for extending out of said predetermined holes and engaging said structure when said fingers penetrate said holes.

7. The combination of claim 1, wherein the heads of said fingers each comprise a conical surface for being engaged by said tool and a shoulder for engaging said structure when said fingers penetrate said predetermined holes.

8. The combination of claim 1, wherein each said head comprises a plurality of shoulders for engaging said structure when said fingers penetrate said predetermined holes, said shoulders being separated by spaces for permitting said heads to collapse to a size smaller than said predetermined holes when said tool engages said heads whereby to disengage said shoulders from said structure.

9. The combination of claim 1, wherein said holes comprise smooth walled cylindrical holes, and said fingers comprise arcs of a cylinder having about the same external diameter as said holes.

* * * * *